(12) United States Patent
Kagermeier et al.

(10) Patent No.: US 7,471,985 B2
(45) Date of Patent: Dec. 30, 2008

(54) HIGH-AVAILABILITY WIRELESS OPERATOR CONTROL DEVICE FOR MEDICAL SYSTEMS

(75) Inventors: Robert Kagermeier, Nürnberg (DE); Michael Krause, Stendal (DE); Donal Medlar, Weisendorf (DE); Dietmar Sierk, Halle (DE)

(73) Assignee: Siemens Aktiengesellschaft, Munich (DE)

( * ) Notice: Subject to any disclaimer, the term of this patent is extended or adjusted under 35 U.S.C. 154(b) by 416 days.

(21) Appl. No.: 10/866,844

(22) Filed: Jun. 14, 2004

(65) Prior Publication Data

US 2005/0004630 A1      Jan. 6, 2005

(30) Foreign Application Priority Data

Jun. 17, 2003   (DE) ............................. 103 27 296

(51) Int. Cl.
*A61N 1/08* (2006.01)
(52) U.S. Cl. ......................................... 607/60; 128/903
(58) Field of Classification Search ................. 128/903, 128/904; 607/30, 32, 60
See application file for complete search history.

(56) References Cited

U.S. PATENT DOCUMENTS 6,574,509 B1 * 6/2003 Kraus et al. .................... 607/60

7,092,761 B1 * 8/2006 Cappa et al. ................... 607/60
2002/0013517 A1 * 1/2002 West et al. .................... 600/300

FOREIGN PATENT DOCUMENTS

DE      297 23 819          4/1999
DE      101 03 302 A1       8/2002

OTHER PUBLICATIONS

German Office Action dated Sep. 28, 2005 with English Translation.

* cited by examiner

*Primary Examiner*—Carl H. Layno
*Assistant Examiner*—Tammie K. Heller
(74) *Attorney, Agent, or Firm*—Brinks, Hofer, Gilson & Lione

(57) ABSTRACT

An apparatus for medical diagnosis and therapy systems has at least one operator control device generating at least one control signal corresponding to at least one function of the apparatus, a control unit for converting the at least one control signal into the at least one function of the medical apparatus, a signal transmission device for wireless transmission of the at least one control signal from the at least one operator control device to the control unit of the medical apparatus, and at least one console adapted for detachably engaging the at least one control device. The signal transmission device has at least one first transmission unit in communication with the at least one operator control device and at least one second transmission unit in communication with the control unit. At least one interference-free transmission path is established when the at least one control device is engaged with the at least one console.

18 Claims, 3 Drawing Sheets

HIGH-AVAILABILITY WIRELESS OPERATOR CONTROL DEVICE FOR MEDICAL SYSTEMS

BACKGROUND

The invention relates, in general, to the control of medical systems, and in particular, to the control of medical systems via mobile, wirelessly-communicating operated control devices.

Medical apparatuses and medical systems are typically understood to be technical equipment used for diagnosis and therapy in the medical field. Medical equipment such as electro-medical devices and nuclear medical devices, X-ray or ultrasound equipment, devices used in medical laboratory technology or the like are primarily used in surgery, intensive care, radiation treatment, and emergency services.

In order to provide flexibility of use, medical systems are often equipped with a wireless mobile operator control device. Radio, infrared, or ultrasonic techniques are the main transmission methods used. The use of a wireless operator control device, however, involves two serious problems.

On one hand, transmission paths between the operator control device and a medical apparatus to be controlled can be negatively influenced by interference signals, making them unreliable to control. Possible interference signals in radio transmission include, for example, radio effects generated by transmitter units, consumer electronics devices, nearby radio control units, or lightning discharges. In infrared transmission, interference signals are essentially comprised of modulated light sources, such as nearby remote control units, light flashes from discharge lamps, or thunderstorm activity. Ultrasonic transmissions are sensitive, among other things, to incident radiation from ultrasound diagnosis units, rinsing baths, and nearby ultrasonic remote control units.

Another problem typically lies in an unreliable supply of energy to the separate mobile operator control device via energy storage devices that are independent of a power grid, such as accumulators or batteries. A limited capacity of these energy storage devices may lead to frequent failures of the mobile operator control device.

Both problems may prevent wireless mobile operator control devices from being used to control medical systems since using them does not guarantee a required or desirable degree of operational reliability. In the past, therefore, wireless mobile operator control devices have typically been used only for non-critical control tasks such as image processing functions. For critical operational functions, the mobile operator control device has been connected to the medical apparatus by means of cable-based, shielded transmission paths. In order to combine flexibility and safety in operation control, critical and non-critical operational functions are currently executed in parallel on both a wireless operator control device and a cable-connected operator control device. The parallel execution of operational functions may incur correspondingly high costs and can also lead to incorrect operation, for example if an unauthorized person manipulates the cable-connected operator control device.

OBJECT AND SUMMARY

The present invention is defined by the appended claims. This description summarizes some aspects of the present embodiments and should not be used to limit the claims.

An object is to disclose a mobile operator control device for medical systems that can be inexpensively produced and offers a substantially high degree of flexibility, reliability, and safety in operation.

A medical apparatus to be controlled may include at least one operator control device, a control unit, a signal unit, and a console. The operator control device may be used to manually trigger at least one control signal. The control unit is designed to convert the at least one control signal into at least one function of the medical apparatus. The signal transmission unit is used to execute the wireless transmission of control signals from the at least one operator control device to the control unit of the medical apparatus; the signal transmission unit includes at least a first transmission unit that is connected to the operator control device and at least a second transmission unit that is connected to the control unit. The at least one operator control device can be attached to and detached from the console of the medical apparatus without the aid of accessories. When attached, at least one interference-free transmission path is produced between the at least first and at least second transmission units of the console and the at least one operator control device.

In one aspect, the at least one interference-free transmission path is advantageously embodied as a shielded conduit in order to minimize interference signals from traveling into the transmission path. In particular, the shielded conduit is advantageously embodied in the form of a waveguide for a transmission of electromagnetic space waves or in the form of an optical waveguide, to reduce external interference with the electromagnetic or optical signal line.

In another aspect, to assure the signal transmission between the operator control device and the console independent of the spatial relationship between the two, the console may have a converter for converting a signal-carrying space wave into a signal-carrying conductor wave and/or vice versa.

In another aspect, preferably, the console has an antenna for inductive energy transmission, which supplies electrical energy to the operator control device attached to the console, particularly when the capacity of the energy storage device disposed in the operator control device has been exhausted. When the operator control device is attached to it, the console may advantageously form a second transmission path for inductive transmission of electrical energy to supply power to the operator control device, which assures the supply of energy to the operator control device when it is attached.

In another aspect, for situational adapted placements, at least one console is connected to the medical apparatus via a cable.

In another aspect, the medical apparatus can advantageously be equipped with a transmission control unit for controlling a transmission path of at least one console. The transmission control unit is preferably equipped so as to convert a transmission path based on electromagnetic signal transmission of a console to an optical or galvanic signal transmission once the corresponding operator control device is attached to the console. In addition, the transmission control unit can be equipped so that when one operator control device is attached to a console, the transmission paths are switched off in other consoles that do not have an operator control device attached to them.

In another aspect, to assure that the medical apparatus can be reset to a safe operating mode when desired, the operator control device is advantageously equipped with a device for triggering an emergency stop function. In addition, the console has a suitable emergency stop device that is designed to trigger an emergency stop function of the medical apparatus in the event of an interruption of a transmission path and/or a malfunction within the operator control device. As such, the console is preferably designed so that attaching the operator control device to the console may cause the emergency stop device of the console to be deactivated.

Illustrative and exemplary embodiments of the invention are described in further detail below with reference to and in conjunction with the figures.

DETAILED DESCRIPTION

Figure 1:
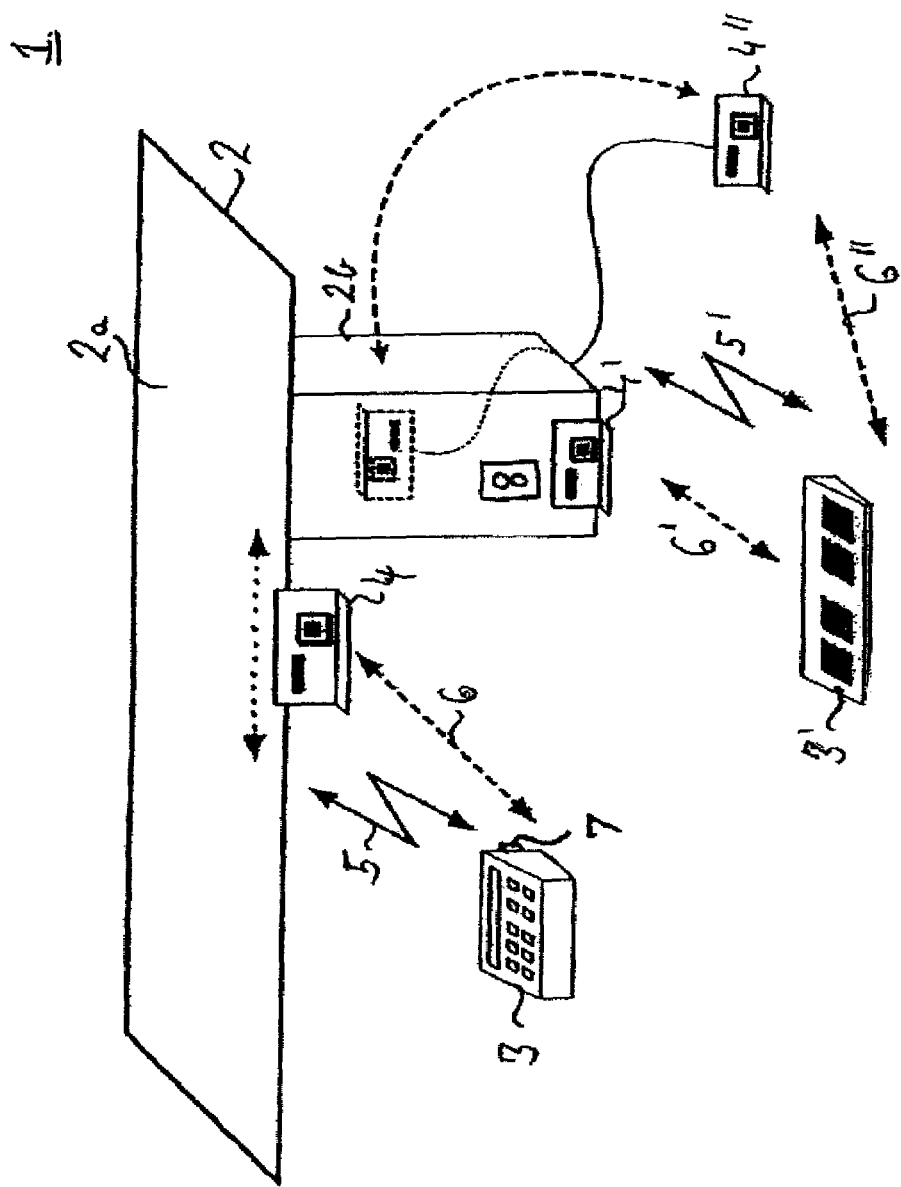
FIG. 1 is a schematic illustrating an embodiment of a medical diagnosis or therapy apparatus with a detachable control device.

While the present invention may be embodied in various forms, there is shown in the drawings and will hereinafter be described some exemplary and non-limiting embodiments, with the understanding that the present disclosure is to be considered an exemplification of the invention and is not intended to limit the invention to the specific embodiments illustrated.

In this application, the use of the disjunctive is intended to include the conjunctive. The use of definite or indefinite articles is not intended to indicate cardinality. In particular, a reference to "the" object or "a" object is intended to denote also one of a possible plurality of such objects.

FIG. 1 shows an embodiment of a medical apparatus I which is also referred to below for short and convenience as the apparatus or device. In a schematic depiction, the medical apparatus has a patient table 2 as used, for example, in medical diagnosis or therapy systems. The patient table is composed of a tabletop 2a and a table base 2b.

The patient table 2 has a console 4 fastened or affixed to it, to which an operator control device 3 can be attached. The console 4 is connected to a housing part of the medical apparatus 2 either in a stationary position or, as depicted by the dotted double arrow in FIG. 1, in a slidingly displaceable fashion. In both cases, the console 4 is fastened to an outside surface of the apparatus 2 to provide a user easy access to it. Alternatively, or in addition, another console 4 can also be disposed separate from the body of the apparatus 2. As such, an electrical connection of the console 4 to the apparatus 2 is achieved via a cable, which may permit a variation of a relative spatial position of the console 4 and apparatus 2 within distal limits prescribed by a length of the cable.

The operator control device 3 may constitute or provide a user interface via which a user, by manipulating control elements such as keys, buttons, or the like, can trigger a generation of control signals. The control signals thus produced are subsequently converted by a control unit 8 of the apparatus 2 so as to initiate a corresponding function of the apparatus 2.

Often a medical system will have a number of operator control devices 3 and 3' that can be actuated independently of one another. Typically, separately located operator control devices 3 are provided for hand and foot actuation. Operator control devices 3 designed for hand operation are usually more complex in design than those for foot operation 3', basic functions that do not generally require any which usually only permit the control of certain particular dexterity.

In order to offer the operator or user of a medical apparatus 2 a greater degree of flexibility in controlling the apparatus 2, an operator control device 3 of the apparatus 2 may be designed as a separate mobile device. The transmission of control signals may then occur in wireless mode. The energy supply to the mobile operator control devices 3 and 3' is preferably maintained by replaceable energy storage devices that are as rechargeable as possible, such as batteries, accumulators, or capacitive storage units, which are disposed inside the respective operator control device 3, 3'.

A signal transmission device (not shown), which may be composed of two spatially separate transmission units, transmits control signals between the operator control device 3 (or 3') and an associated console 4 (or 4'). A first of these transmission units is connected to the operator control device 3, (3') and is equipped to transmit control signals generated by the operator control device 3, (3'). The second transmission unit is disposed spatially in the vicinity of the console respectively associated with it. The second transmission unit receives the control signals transmitted by the first transmission unit and forwards them to the control unit of the apparatus 2.

The operator control device 3 (3') can be attached to the console 4 (4') without any additional accessories, i.e. without the aid of tools. As such, a part of the surface of the console 4 (4') is suitably embodied and adapted so as to engagingly produce a-snap connection or a clamping connection, which is detachable, with a corresponding part of the surface of the operator control device 4 (4'). Alternatively, the detachable connection can also be produced via a simple locking mechanism or also via a magnetic or textile adhesive connection, for example a hook-and-loop attachment. In an alternate instance, a tab-and-socket connection is provided.

Figure 2:
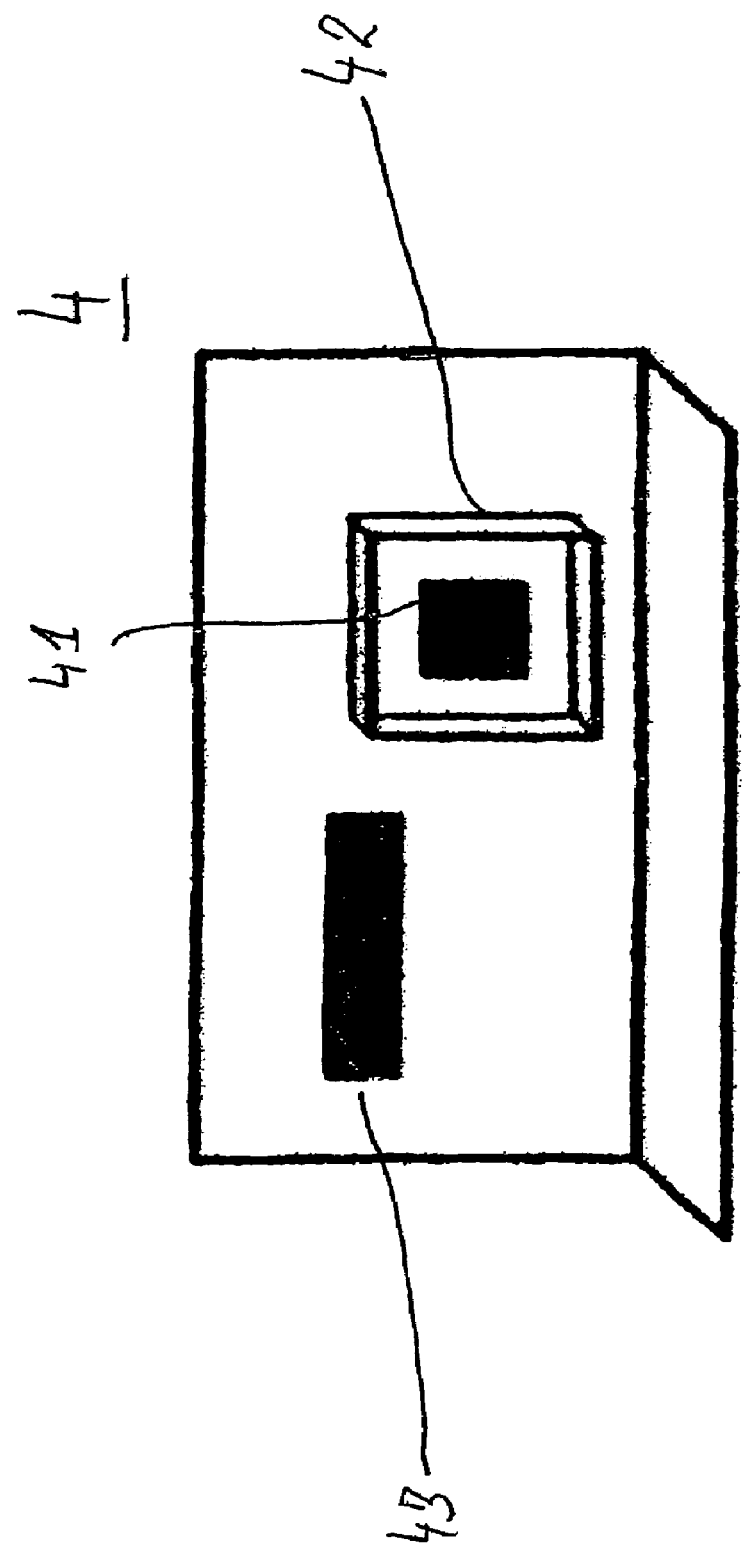
FIG. 2 is a schematic illustrating a detailed embodiment of a console of the medical apparatus according to FIG. 1.

FIG. 2 shows a console 4. The console 4 has a receiving system 41 for receiving or detecting control signals from the first transmission unit. The receiver unit 41 may include a converter for converting a signal-carrying space wave into a corresponding signal-carrying conductor wave, which conveys the control signals transmitted from the operator control device 3 to an electronic or optoelectronic signal processing unit (not shown). Depending on a type of wireless transmission, the receiver unit 41 may be embodied as an antenna for electromagnetic radiation, as an ultrasonic converter, an optocoupler, or as a lens for coupling a light signal into an optical waveguide. If the transmission path between the operator control device 3 and the console 4 is equipped for a two-way communication, then the converter 41 may be embodied as a transmitter/receiver unit that also executes a corresponding conversion of a conductor wave into a space wave.

The transmitter unit or the transmitter/receiver unit 7 may be disposed in the operator control device 3 to be positioned directly opposite the converter 41 when the operator control device 3 is attached to the console 4. A frame 42 on the console 4 closes the space between the converter 41 and the operator control device 3 in relation to the outside. The spatial relationship between the converter 41 and the operator control device 3 may produce a conduit that is shielded in relation to the outside, which assures an interference-free wireless transmission between the operator control device 3 and console 4.

The interference-free transmission path can be embodied by suitably dimensioning the frame 42 in relation to the waveguide for electromagnetic signals, with a favorable conductivity for a corresponding transmission frequency used and a powerful damping of other frequencies.

With a use of an optical, e.g. infrared, transmission, the frame 42 is part of an optical plug connector (not shown) so that an optical waveguide constitutes the transmission path of the shielded conduit.

If there are interference signals 5 and 5', as shown in FIG. 1 that may hinder a reliable remote control of the medical apparatus 1, then the operator control device 3 is attached to the console 4. The frame 42 then shields the transmission path 6 from external influences, which substantially assures an interference-free operation.

The receiver and/or transmitter/receiver unit 41 can also be adapted to more than one transmission method. For example, it can have an antenna for the electromagnetic signal transmission and an optocoupler for an optical signal transmission. When the operator control device 3 is attached to the console 4, a transmission control unit then switches the apparatus 1 for example from the electromagnetic signal transmission to an optical signal transmission. If the converter 41 is equipped with electrical contacts, then the signal transmission can alternatively also be converted to a galvanic signal transmission, for example by means of a plug contact connection.

In order to further increase an availability of the operator control device 3, the console 4 is preferably also provided with a charging unit 43 in order to charge the energy storage device(s) of the operator control device 3 when attached to the console 4. The energy transmission preferably occurs in a contactless manner, e.g. by means of electromagnetic induction to minimize malfunctions due to bent, oxidized, or soiled contacts, for example. As such, an antenna 43 for inductive energy transmission is attached to a surface of the console 4. In alternate embodiments, the energy transmission may occur in parallel or alternatively to the inductive transmission, via a galvanic connection produced via contacts.

If the medical apparatus 1 is provided with a number of independently actuatable operator control devices 3, then an interference signal 5 or 5' via each of the associated transmission conduits 6, 6', or 6", as shown if FIG. 1, can trigger an undesirable reaction of the apparatus 1. If a user who has recognized that such an interference is occurring attaches one of the operator control devices 3 to the console 4, the interference signals 5 or 5' continue to be received via the receiver units of the other consoles and can potentially lead to critical situations or undesirable malfunctions.

To minimize these undesirable malfunctionse, the above-mentioned transmission control unit of the medical apparatus 1 can be designed so that when an operator control device 3 is attached to a console 4, the transmission paths via the other consoles 4 are deactivated until the respective associated operator control device 3 is attached to them. In addition, the deactivation of the transmission conduits can also be executed by a user via a function of the operator control device 3.

A safety concept of a large number of medical apparatuses 1 provides for a fixed-wire safety circuit for controlling safety-critical functions, e.g. a movement of the apparatus 1, a triggering of radiation, or a triggering of a shock wave. The safety circuit is provided with a so-called emergency stop switch, which affords a user—in a manner similar to that of an emergency shut-off switch—the possibility of resetting the apparatus 1 back into a safe operating mode in the event of a critical operating state.

Figure 3:
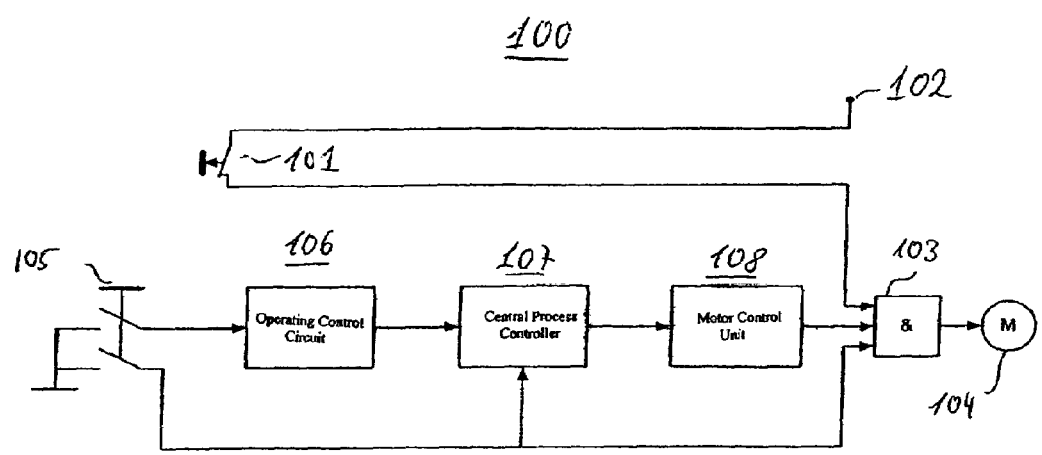
FIG. 3 is an illustrative block diagram of a motor control unit with a hard-wired safety circuit for the medical apparatus of FIG. 1.

A block circuit diagram 100 in FIG. 3 shows a motor control unit with a hard-wired safety circuit for a medical apparatus 1. A particular function of the motor 104, e.g. for moving a patient tabletop, is triggered via a control element 10.5 on the apparatus 1. The input control element 105 is generally embodied with two channels in order to increase the operational reliability of the system. The depiction of the control element 105 in FIG. 3 as a two-channel, normally open contact, however, is understood to be merely an example. Usually, a number of control elements are provided in order to control several possible functions of an apparatus 1. Examples of possible functions may include forward and backward travel, speed, or rotation speed of the motor 104, or the like.

Respective states of the input element 105 are digitally converted by an operating control circuit 106 and are supplied to a central process controller 107 on a first of the two-channels. A signal originating from a second channel of the control element 105 is supplied to the process controller 107 in parallel as a way of monitoring the signals originating from the first channel. The signals processed by the process controller 107 are forwarded to a motor control unit 108 whose output signals activate the motor 104 in accordance with the triggered function. The operating control circuit 106, the process controller 107, and the motor control unit 108 are preferably designed as programmable electronic components.

The safety circuit may perform two tasks. In one task, a check is run as to whether the respective control signal for the motor 104 is actually a result of a corresponding actuation of the control element 105. In the example shown, the check is achieved with a two-channel input device 105. Only if a state of the second channel is in the correct relation with a state of the first channel is the control signal forwarded from the motor control unit 108 to the motor 104. Otherwise, an AND gate 103 shown in the example of FIG. 3 prevents the control signal from being forwarded to the motor 104. In addition, as already been mentioned, an additional control is executed with the aid of the second channel in the process controller 107.

A second task performed by the safety circuit is to provide an emergency function for manually resetting the apparatus 1 back to a safe operating mode. As such, an emergency stop switch 101, preferably embodied as a normally closed contact, is provided, which connects a control potential-carrying terminal 102 to an input of the AND gate 103. An actuation of the emergency stop switch 101 breaks this connection, as a result of which the AND gate 103 prevents the output signals of the motor control unit 108 from being forwarded to the motor 104.

The emergency stop switch 101 is usually disposed in the immediate vicinity of the control console 4 so that, for example in the event of an uncontrolled movement of the apparatus 1, an intervention can be executed immediately, with substantially no delay. But if the medical apparatus 1 is being controlled via a remote control, then the person operating it may first run to the apparatus 1 before being able to actuate the emergency stop switch 101.

In a preferred embodiment of a wireless remote controllable apparatus 1, the operator control device 3 is provided with a control element 105 that triggers a control signal for an emergency stop function when actuated. In order to assure a readiness of a corresponding remotely triggerable emergency stop function, the availability of this function may be checked regularly. The regular check can be achieved through a kind of dead man's signal that the operator control device 3 (3') transmits to the associated console 4 (4') at regularly repeating intervals.

A substantially greater operational reliability may be achieved by having the transmission unit of the console 4 regularly send an inquiry signal to the receiving unit of the console 4 which, when the emergency stop function is available, responds by sending back a confirmation signal. As such, the transmission path between the console 4 (4') and operator control device 3 (3') is suitably embodied as bidirectional, i.e. the transmission units of both the console 4 and the operator control device 3 are embodied as combined transmitter/receiver units.

The availability of the emergency stop function is easy to test in that when the emergency stop control switch 101 is not actuated; a uniquely identifiable electrical or electronic state is assured that changes in the event of both an actuation and a possible malfunction. Alternately, the emergency stop function is embodied as a closed circuit with a control element that is embodied as a normally closed contact. The readiness is tested by checking a current flow or a potential transmission in the circuit. An actuation of the normally closed contact breaks the circuit and thus triggers the emergency stop function.

If the energy supply of the operator control device 3 (3') is exhausted, then little or no current flows and the testable potential changes, which results in a physical state that represents the unavailability of the emergency stop function. If the transmission unit is still functioning, then this unavailability of the console 4 is actively displayed.

In order to prevent injury to patients and/or operating personnel, it is necessary to guarantee a reset of a medical apparatus 1 back to a safe operating mode. In a dangerous situation, however, a nonfunctional emergency stop function of a wirelessly controlled operator control device 3 or 3' could result in unacceptable delays in an emergency stopping action. The unavailability of the emergency stop function in the operator control device 3 or 3' is therefore treated by the console 4 as a triggered emergency stop function, thus preventing a nonfunctioning emergency stop triggering device from being left in place, which, in a dangerous situation, would delay a reaction time of the operating personnel.

An emergency stop triggered in the above described preventive manner is useful when attaching the operator control device 3 (3') to the console 4 as described above, unless the emergency stop function is actually active in the remote control 3. A textual or light indicative display on the operator control device 3 can contain or indicate a corresponding request that the operating personnel attach the remote control 3 to the console 4 of the apparatus.

Figure 4:
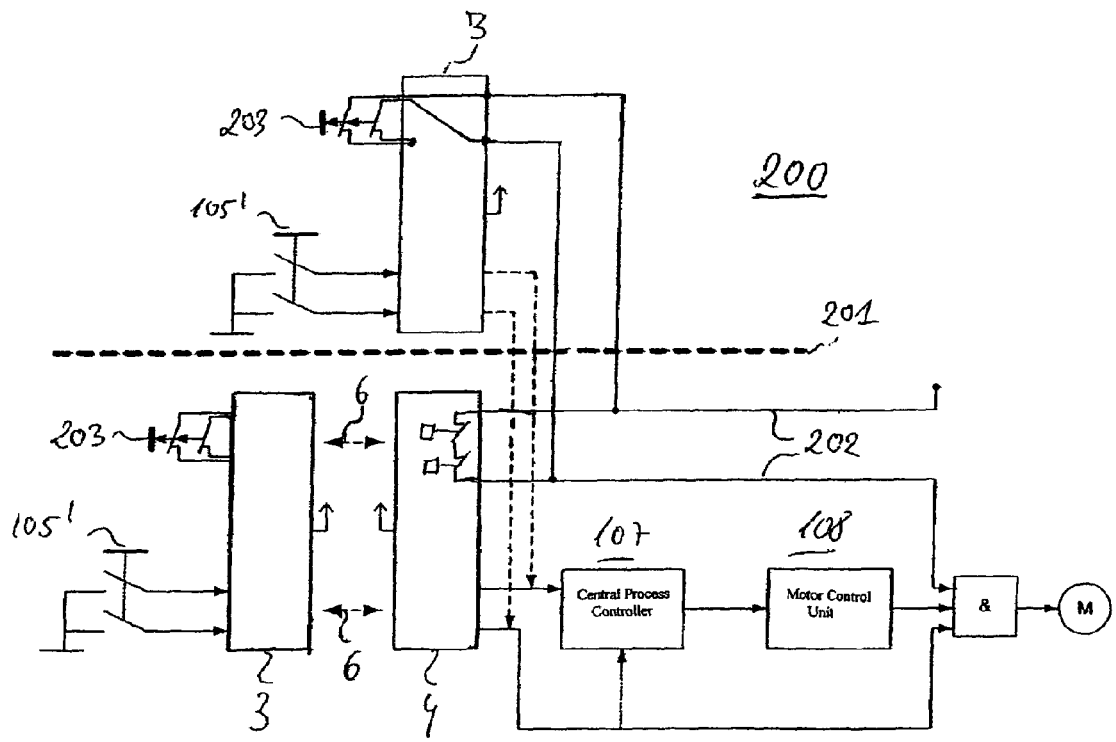
FIG. 4 is an illustrative block circuit diagram of a motor control unit with a hard-wired safety circuit for the medical apparatus of FIG. 1 and a wireless operator control device.

Referring to FIG. 4, an embodiment of such a safety circuit 200 for a wireless operator control device 3 is shown, with a correspondingly embodied emergency stop function. As shown, the region below the bold dashed line 201 depicts the normal state, i.e. a remote control of the medical apparatus 1 is possible since no malfunctions are occurring in either the remote control 3 itself or the transmission path 6.

In the event of a malfunction, the operator control device 3 is attached to the console 4 in the manner described above. The attachment assures a reliable connection between the two, which bypasses an emergency circuit 202 of the console 4 and transfers the emergency stop function currently in the remote control device 3 to the console 4.

Referring to FIG. 4, a galvanic coupling between the control element 3 and the console 4 is shown. When the remote control device 3 is attached to the console 4, an emergency stop switch 203 of the operator control device 3 is connected in parallel to the emergency circuit 202. If the emergency stop switch 203 on the operator control device 3 is not actuated, then this switch 203 closes the emergency circuit of the console 4 and resets the medical apparatus I back to the normal operating state. As indicated for a motor switch 105', a control by means of control elements of the console 4 is correspondingly replaced by the remote control 3.

The combination according to the invention of an easy-to-produce transmission channel, which is shielded from interfering influences, with a contactless energy transmission produces a high-availability wireless, mobile operator control device 3 for medical apparatuses 1, which has a low degree of technical complexity. An integration of an emergency stop function into the mobile operator control device 3 additionally guarantees short reaction times of the operating personnel in dangerous situations, even in the event of interference in the transmission path or malfunctions in the operator control device 3.

The invention claimed is:

1. A system for medical diagnosis or therapy, the system comprising:
   an apparatus for medical diagnosis or therapy system, the apparatus including a control unit operable to convert at least one control signal into at least one function of the apparatus;
   at least one operator control device operable to generate the at least one control signal corresponding to the at least one function of the apparatus;
   a signal transmission device for wireless transmission of the at least one control signal from the at least one operator control device to the control unit; and
   at least one console adapted for detachably engaging the at least one control device, the at least one console being attached to the apparatus,
   wherein the signal transmission device has at least one first transmission unit in communication with the at least one operator control device and at least one second transmission unit in communication with the control unit, and
   wherein a wireless transmission path is between the at least one operator control device and the at least one console, the wireless transmission path being a substantially interference-free transmission path inside a shielded conduit between the at least one operator control device and at least one console.

2. The system of claim 1, wherein a waveguide for transmitting electromagnetic waves is the shielded conduit.

3. The system of claim 1, wherein an optical waveguide is the shielded conduit.

4. The system of claim 1, wherein the at least one console has an antenna for inductive energy transmission.

5. The system of claim 4, wherein the at least one console and the at least one operator control device, when engaged with each other, form a second transmission path for the inductive transmission of electrical energy for supplying current to the operator control device.

6. The system of claims 1, wherein the at least one console is connected to the operator control device via a cable.

7. The system of claim 1, wherein a transmission control unit is provided for controlling the wireless transmission path.

8. The of claim 7, wherein the transmission control unit convert an electromagnetic signal transmission of the at least one console to an optical or galvanic signal transmission when the at least one operator control device is engaged with the corresponding at least one console.

9. The system of to claim 8, wherein, when the at least one operator control device is engaged with the at least one console, the transmission control unit switches off transmission paths corresponding to consoles that are not engaged with operator control devices.

10. The system of claim 1, wherein the at least one operator control device has a unit for triggering an emergency stop function.

11. The system of claim 10, wherein, the at least one console has an emergency stop device designed to trigger an emergency stop function of the apparatus for at least one of:

a detection of an interference in a transmission path, a malfunction of the operator control device or combinations thereof.

12. The system of claim 10, wherein the emergency stop function is provided via an electrical circuit with the control element being a normally closed contact.

13. The system of claim 1, wherein the at least one operator control device has a safety circuit with a corresponding emergency stop switch.

14. The system of claim 1, wherein the at least one console is adapted for accessory-free attachment with the at least one operator control device.

15. The system of claim 1, wherein the at least one console has a converter for converting a signal-carry wave into a signal-carry conductor wave and/or vice versa.

16. The system of claim 15, wherein the console has an antenna for inductive energy transmission.

17. The system of claim 15 wherein a transmission control unit is provided for controlling the substantially interference-free transmiddion path of the at least one console.

18. The system of claim 17 wherein the at least one operator control device has a unit for triggering an emergency stop function.

* * * * *

UNITED STATES PATENT AND TRADEMARK OFFICE
CERTIFICATE OF CORRECTION

PATENT NO. : 7,471,985 B2
APPLICATION NO. : 10/866844
DATED : December 30, 2008
INVENTOR(S) : Robert Kagermeier et al.

Page 1 of 1

It is certified that error appears in the above-identified patent and that said Letters Patent is hereby corrected as shown below:

In column 8, claim 6, line 47, after "system of" delete "claims" and substitute --claim-- in its place.

In column 8, claim 11, line 65, immediately after "claim 10", wherein" delete "," (comma).

In column 10, claim 17, line 8, delete "transmiddion" and substitute --transmission-- in its place.

Signed and Sealed this

Ninth Day of June, 2009

JOHN DOLL
*Acting Director of the United States Patent and Trademark Office*